(12) United States Patent
Boehm et al.

(10) Patent No.: US 6,271,518 B1
(45) Date of Patent: Aug. 7, 2001

(54) PROCESS FOR DETECTING AND CHARACTERIZING FORMATION HYDROCARBONS

(75) Inventors: Claudine Boehm, Beuste; Jean-Bernard Berrut, Pau, both of (FR)

(73) Assignee: Elf Exploration Production (FR)

( * ) Notice: Subject to any disclaimer, the term of this patent is extended or adjusted under 35 U.S.C. 154(b) by 0 days.

(21) Appl. No.: 09/222,720

(22) Filed: Dec. 29, 1998

(30) Foreign Application Priority Data

Dec. 30, 1997 (FR) .................................................. 97 16711

(51) Int. Cl.⁷ ...................................................... G01V 5/00
(52) U.S. Cl. ..................... 250/255; 250/461.1; 250/459.1
(58) Field of Search .............................. 250/255, 461.1, 250/459.1

(56) References Cited

U.S. PATENT DOCUMENTS

| | | | |
|---|---|---|---|
| 4,609,821 | 9/1986 | Summers | 250/255 |
| 4,783,416 | 11/1988 | Patel | 436/60 |
| 4,814,614 | 3/1989 | Tsui | 250/301 |
| 4,865,746 | 9/1989 | Overfield | 210/656 |
| 4,959,549 | 9/1990 | Haub et al. | 250/461.1 |
| 4,988,446 | 1/1991 | Haberman et al. | 210/656 |
| 5,076,909 | 12/1991 | Overfield et al. | 208/177 |

*Primary Examiner*—Constantine Hannaher
*Assistant Examiner*—Andrew Israel
(74) *Attorney, Agent, or Firm*—Blank Rome Comisky & McCauley, LLP

(57) ABSTRACT

The present invention relates to the exploration for and exploitation of formation hydrocarbons. According to the invention, a sample of material, representative of the impregnation with hydrocarbons of the rocks passed through, is taken during a drilling operation, with which sample a value of an emission flux, representative of the concentration of the fluorescent elements in the sample, and a value of a fluorescence quotient, which reflects the nature of the hydrocarbons present in the sample, are determined by spectrofluorimetry. The invention finds its application in analytical laboratories and on the drilling sites of petroleum production fields.

9 Claims, 4 Drawing Sheets

PROCESS FOR DETECTING AND CHARACTERIZING FORMATION HYDROCARBONS

DESCRIPTION

1. Technical Field

The present invention relates to the exploration for and exploitation of formation hydrocarbons.

This invention finds its application in analytical laboratories and on the drilling sites of petroleum production fields.

2. Prior Art

Drilling operations for the exploration for hydrocarbons in underground formations are long and expensive.

One means for reducing the duration and cost of these operations is to optimize the detection of the formation hydrocarbons in all drilling conditions.

This optimization consists in recognizing all the impregnated rocks and in directing the test programme so as to accurately define the zones to be tested.

Document EP 0,344,950 describes a method for determining the amount of hydrocarbons present in an underground formation, which consists in carrying out the following steps:

taking a rock sample, extracting the hydrocarbons contained in a known amount of the rock sample, using a known amount of a solvent, exciting the extract obtained with ultra-violet radiation of a wavelength at which most of the hydrocarbon mixtures are fluorescent, this wavelength being between 250 and 310 nanometers, recording, using a fluorimeter, the radiation emitted by the extract at a given wavelength, determining the amount of fluorescent elements present in the rock sample by comparing the intensity of the radiation recorded with the radiation emitted at the same wavelength by samples of materials containing known amounts of hydrocarbons.

Since the rock sample is impregnated with both the formation hydrocarbons and the fluorescent elements which form part of the composition of the drilling mud, the results obtained by this method are inaccurate. Furthermore, they give no information regarding the nature of the fluorescent elements detected, most particularly in the case of oily muds.

DESCRIPTION OF THE INVENTION

The aim of the present invention is, precisely, to overcome these drawbacks and to provide a process for detecting and characterizing formation hydrocarbons.

This process can be used in the laboratory and on the drilling sites of petroleum production fields.

To this end, the present invention proposes a process for detecting and characterizing formation hydrocarbons which consists in carrying out the following steps:

taking a sample of material which is representative of the rocks passed through during a drilling operation, taking a determined amount of material to be analysed from the said sample of material, extracting the hydrocarbons contained in the said amount of material to be analysed, using a known amount of a solvent for hydrocarbons, in order to make up an initial extract, characterized in that it also consists in carrying out the following operations:

diluting the initial extract by a factor d in order to obtain a final extract, exciting the final extract with ultraviolet radiation of a wavelength chosen within the band substantially between 250 and 400 nanometers, recording, in a wavelength band L, an emission spectrum resulting from the excitation of the final extract, calculating the emission flux of the sample of material by applying the following formula:

$$FLUX = d * \sum_{i=1}^{n} I(\lambda i)$$

in which

FLUX represents the emission flux of the sample of material $I(\lambda i)$ represents the intensity of the radiation emitted at a wavelength $\lambda i$ of the band L by the final extract, n represents the number of wavelengths of the emission spectrum sampled at a pitch of between 1 and 20 nanometers, and is equal to L divided by the pitch, i ranges from 1 to n, the value of the emission flux of the sample of material is proportional to the concentration of fluorescent elements in the sample of material, including, in particular, the formation hydrocarbons, calculating the fluorescence quotient of the sample of material using the following formula:

$$FQ = \text{area } A/\text{area } B$$

in which:

FQ represents the fluorescence quotient of the sample of material, area A and area B are calculated, respectively, by the following formulae:

$$\text{Area } A = \sum_{i=x+1}^{n} I(\lambda i)$$

$$\text{Area } B = \sum_{i=1}^{x} I(\lambda i)$$

in which:

$I(\lambda i)$ and n are defined as above, x is an integer between 1 and n, the value of the fluorescence quotient of the sample of material is representative of the nature of the hydrocarbons contained in the sample of material.

According to another characteristic of the process of the invention, the solvent for hydrocarbons is preferably cyclohexane.

According to another characteristic of the process of the invention, the wavelength band L is preferably substantially between 280 and 500 nanometers.

According to another characteristic of the process of the invention, the value x corresponds to the reference point of a wavelength $\lambda x$ substantially equal to 367 nanometers, which is representative of the cutoff between the spectra emitted, on the one hand, by the monoaromatic and biaromatic hydrocarbons and by a portion of the triaromatic hydrocarbons, and, on the other hand, by the polyaromatic hydrocarbons.

According to another characteristic of the process of the invention, a low value of the fluorescence quotient of the sample of material indicates the presence of light hydrocarbons in the said sample and a high value indicates the presence of heavy hydrocarbons.

According to another characteristic, the process of the invention consists in taking a series of samples of material at different depths during the drilling, in determining the fluorescence quotient and the emission flux of each sample, and then in plotting the curves representing the said fluorescence quotient and the said emission flux as a function of the depths, of the variations of the fluorescence quotient and of the emission flux, thus making it possible, respectively, to characterize the nature of the fluorescent elements and to assess the degree of concentration of the said elements in the series of samples of material.

According to another characteristic of the process of the invention consists in comparing the fluorescence quotient of at least one sample of material with the fluorescence quotient of at least one sample of reference product determined in the same way as the fluorescence quotient of the sample of material.

According to another characteristic of the process of the invention, since the drilling is carried out with an injection of mud, the sample of reference product consists of a sample of mud taken during the drilling.

According to another characteristic of the process of the invention, a fluorescence quotient value for a sample of material which is close to the value of the fluorescence quotient for the sample of mud taken during the drilling indicates the absence of formation hydrocarbons in the sample of material, and a different value indicates a presence, if, furthermore, the value of the emission flux for the sample of material is high.

BRIEF DESCRIPTION OF THE DRAWINGS

The invention will be understood more clearly with the aid of the description which follows, and of an embodiment given by way of example and with reference to the attached drawings, in which.

DETAILED DESCRIPTION OF THE INVENTION

In general, the process of the invention is used to detect and characterize formation hydrocarbons.

This process consists in taking some of the cuttings, at different depths during a drilling operation, in order to make up a series of samples of material representing the rocks passed through, followed, after drying and grinding each sample, in taking a determined amount of material to be analysed, in extracting, using a known amount of cyclohexane, the hydrocarbons contained in the amount of material to be analysed obtained from each sample, in order to make up a series of initial extracts. These initial extracts are then diluted by a dilution factor d in order to obtain final extracts. The factor d is determined experimentally for each sample, such that the hydrocarbon concentrations in the final extracts are within the measuring range of the spectrofluorometer subsequently used.

The use of cyclohexane as a solvent for the hydrocarbons is particularly advantageous since it promotes the extraction of the representative polyaromatic compounds in the recoverable formation hydrocarbons, whereas aliphatic solvents are more restricting and chlorinated solvents also dissolve the heavy and polar hydrocarbons which are less mobile and thus more difficult to recover.

Each final extract is introduced into a spectrofluorometer, in which it is excited with ultraviolet radiation of wavelength equal to 265 nanometers. This wavelength is chosen on account of the known property of the hydrocarbons thus irradiated to emit by fluorescence. This wavelength also has the advantage of maximizing the fluorescence emission of the formation hydrocarbons and of minimizing that of the hydrocarbons contained in the oily muds.

The intensity of the radiation emitted by fluorescence by each final extract is recorded using a spectrofluorometer over a significant wavelength band L of between 288 and 498 nanometers.

Figure 1:
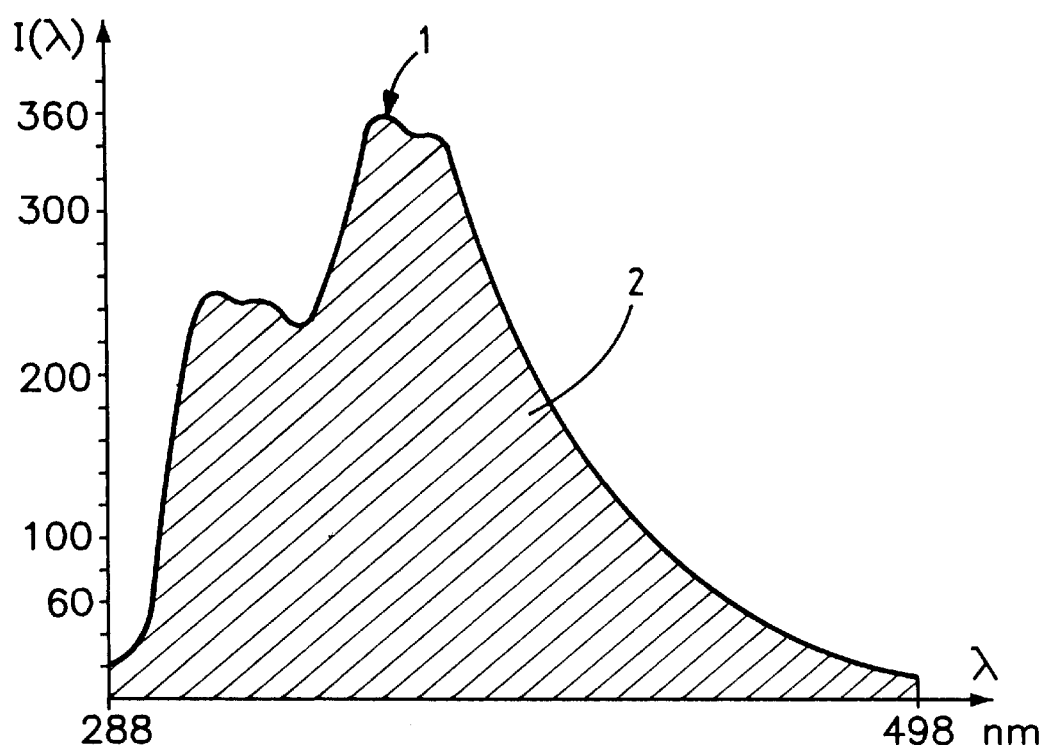
FIG. 1 represents a fluorescence emission spectrum of a final extract obtained from a sample of material.

A spectrum $I(\lambda)$ such as the one in FIG. 1, which represents the variations in the intensity of the radiation emitted by fluorescence as a function of the emission wavelength $\lambda$, is thus obtained for each final extract. The shape of this spectrum is the direct signature of the nature of the fluid which impregnates the rocks in the zone from which the sample of material was taken.

The emission flux of each sample of material is then calculated by applying the following formula:

$$FLUXp = d * \sum_{i=1}^{n} Ip(\lambda i)$$

in which:
  a FLUXp represents the emission flux of the sample taken at the depth p,
  $Ip(\lambda i)$ represents the intensity of the radiation emitted, by the final extract obtained from the sample taken at the depth p, at a wavelength $\lambda i$ of the band L of between 288 and 498 nanometers,
  n represents the number of wavelengths of the emission spectrum sampled at a pitch of 1 nanometre, and is equal to the recording bandwidth of the spectrum, i.e. 498 minus 288 divided by the pitch, i.e. 210,
  i ranges from 1 to n.

The value FLUXp is proportional to the concentration of fluorescent elements, including, in particular, the formation hydrocarbons, contained in the sample of material taken at the depth p.

In the diagram in FIG. 1, the emission flux value of the sample of material is represented by the area 2 of the spectrum, i.e. the shaded area between the curve $I(\lambda)$ and the axis $\lambda$.

It is important to note that, if the FLUXp value thus obtained is considered alone, no information is gained regarding the nature of the elements causing the radiation emitted by fluorescence, and that it is thus impossible to deduce therefrom with certainty that what we are dealing with is formation hydrocarbons.

Figure 2:
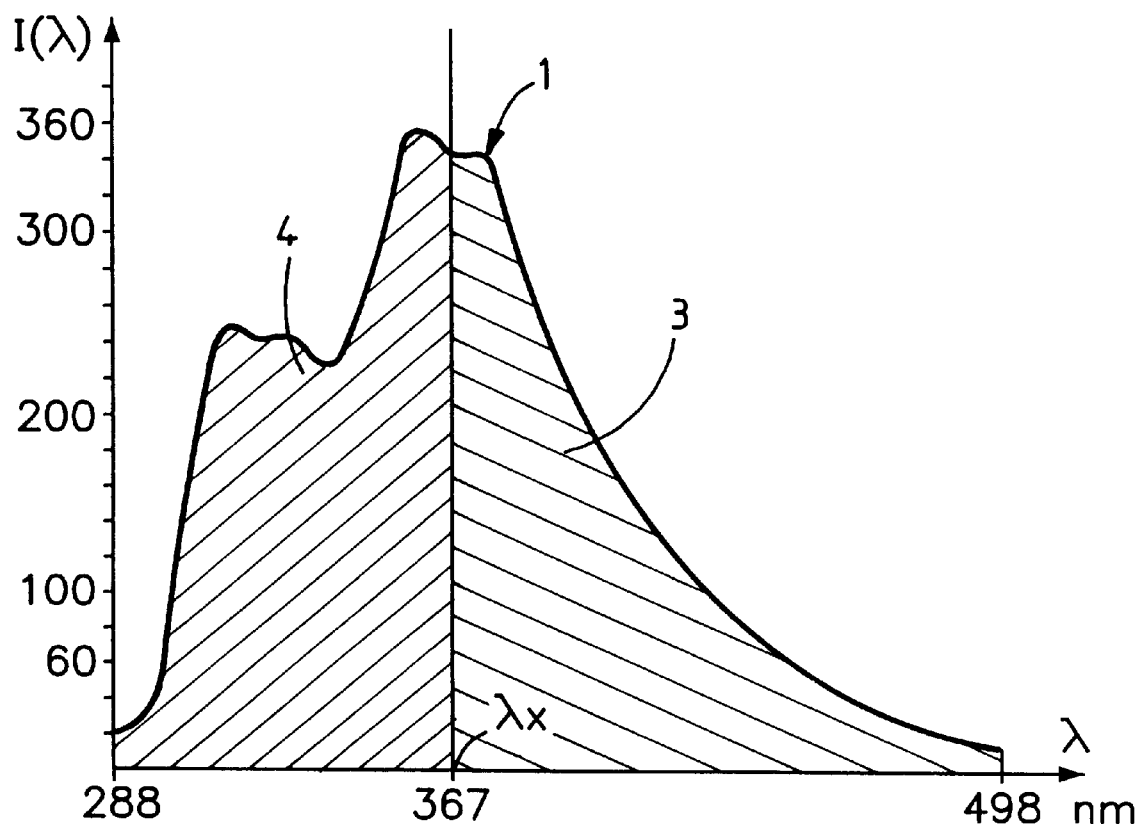
FIG. 2 represents a fluorescence emission spectrum of a final extract obtained from a sample of material, with indication of the wavelength $\lambda x$.

The fluorescence quotient of the sample of material is then calculated by applying the following formula:

$$FQp = \text{area } Ap/\text{area } Bp$$

in which:

FQp represents the fluorescence quotient of the sample of material taken at the depth p, area A and area B are calculated, respectively, by the following formulae:

$$\text{Area } Ap = \sum_{i=x+1}^{n} Ip(\lambda i)$$

represented by area 3 on FIG. 2

$$\text{Area } Bp = \sum_{i=1}^{x} Ip(\lambda i)$$

represented by area 4 on FIG. 2 in which:

$Ip(\lambda i)$ and n are defined as above, x is equal to 79; this value corresponds to the wavelength reference point $\lambda x=367$ nanometers, which is representative of the cutoff between the spectra emitted, on the one hand, by the monoaromatic and biaromatic hydrocarbons and by a portion of the triaromatic hydrocarbons, and, on the other hand, by the polyaromatic hydrocarbons, including another portion of triaromatic hydrocarbons.

The fluorescence quotient of the sample of material is equal to the ratio of the areas 3 and 4 in FIG. 2.

In the same way, the fluorescence quotient FQb of a sample of drilling mud taken at the start of the drilling operation is determined.

If the fluorescence quotient FQp of a sample of material is different from the fluorescence quotient FQb of the mud and if the value FLUXp of the emission flux of the same sample is high, this means that formation hydrocarbons are present at the depth p.

If FQp is close to FQb and if the value FLUXp of the emission flux of the same sample is low, this means that there are no formation hydrocarbons at the depth p.

Similar values of fluorescence quotients FQp obtained from samples of material taken at different depths mean that the hydrocarbons detected are of similar nature.

Different values of fluorescence quotients FQp obtained from samples of material taken from different depths mean that the hydrocarbons detected at these depths are of different nature.

The emission flux values at the different depths reflect the concentration of formation hydrocarbons present in the rocks passed through.

Thus, the process of the invention makes it possible to characterize relatively the nature of the fluorescent elements extracted from the samples of material taken at different depths and to evaluate the concentration thereof in all drilling conditions and particularly in the case of drilling in oily mud.

By means of the invention, all the zones passed through which are impregnated with hydrocarbons are detected without any risk of confusion with the zones which are not impregnated.

The embodiment of the process of the invention which is described above is given by way of non-limiting example, in particular as regards the choice of the material representative of the rocks passed through during the drilling operation, which may advantageously come from core samples or from wall samples.

EMBODIMENT OF THE PROCESS OF THE INVENTION

A series of core samples representing the rocks passed through is taken during an aqueous-mud drilling operation.

One gram of material which constitutes a sample representing the rock passed through at a given depth p is taken from a core sample. This sample is placed in a ceramic crucible and dried in an oven at 50° C. for 30 minutes.

It is then ground manually using an agate mortar. 200 mg of the ground sample of material are then taken and placed in a 50 ml test tube with a ground-glass stopper.

In order to extract the hydrocarbons contained in this amount thus determined of material, 10 ml of cyclohexane are poured into the test tube, which is shaken by hand for 20 seconds.

The ground material/cyclohexane mixture is left to stand for about 10 minutes.

The liquid part of this mixture constitutes the initial hydrocarbon extract.

Some of this initial extract is diluted by a factor d=50 by adding 10 ml of cyclohexane to 200 microlitres of filtered extract, obtained using a 1 ml syringe fitted at the end with a disposable filter.

This solution constitutes the final extract, some of which is transferred into a cuvette of an LS50B spectrofluorometer manufactured by the company Perkin Elmer.

The final extract is excited using ultraviolet radiation of wavelength equal to 265 nanometers with a bandwidth of 15 nanometers.

The crude spectrum of the radiation emitted by fluorescence by the final extract is recorded, i.e. the values of the intensity of the radiation emitted in the 288 to 498 wavelength band L is recorded at a rate of 120 nm/minute, through a bandwidth window of 5 nm.

The crude spectrum recorded is then transferred onto a Digital 466 microcalculator connected to the spectrofluorometer.

An analytical blank is carried out by applying the same procedure as above without the sample of material.

The blank spectrum thus obtained is subtracted from the crude spectrum to give the emission spectrum $I(\lambda i)$, from which the emission flux is calculated by applying the following formula:

$$FLUXp = dp * \sum_{i=1}^{n} Ip(\lambda i)$$

in which:

FLUXp represents the emission flux of the sample taken at the depth p, dp represents the dilution factor of the initial extract of the sample taken at the depth p, $Ip(\lambda i)$ represents the intensity of the radiation emitted by the final extract, at a wavelength $\lambda i$ of the band L of between 288 and 498 nanometers, n represents the number of wavelengths of the emission spectrum sampled at a pitch of 1 nanometre, which is equal to the recording bandwidth of the spectrum, i.e. 498 minus 288 divided by the pitch, i.e. 210, i ranges from 1 to n.

The fluorescence quotient of the sample taken at the depth p is then calculated by applying the following formula:

$$FQp = \text{area } Ap / \text{area } Bp$$

in which:

FQp represents the fluorescence quotient of the sample of material taken at the depth p, area Ap and area Bp are calculated, respectively, by the following formulae:

$$\text{Area } Ap = \sum_{i=x+1}^{n} Ip(\lambda i)$$

$$\text{Area } Bp = \sum_{i=1}^{x} Ip(\lambda i)$$

in which:

Ip(λi) and n are defined as above,
x is equal to 79.

This sequence of operations is repeated using samples taken at different depths from the core drillings carried out.

For the samples whose maximum intensity of emitted radiation exceeds the value 800, the solution must be rediluted.

Thus, for the samples p1 and p7, the dilution factors are 167 and 125, respectively.

The results presented in the table below are obtained.

In this table, P means the depth at which the sample is taken during the drilling and NS indicates a value which is not significant.

Figure 3:
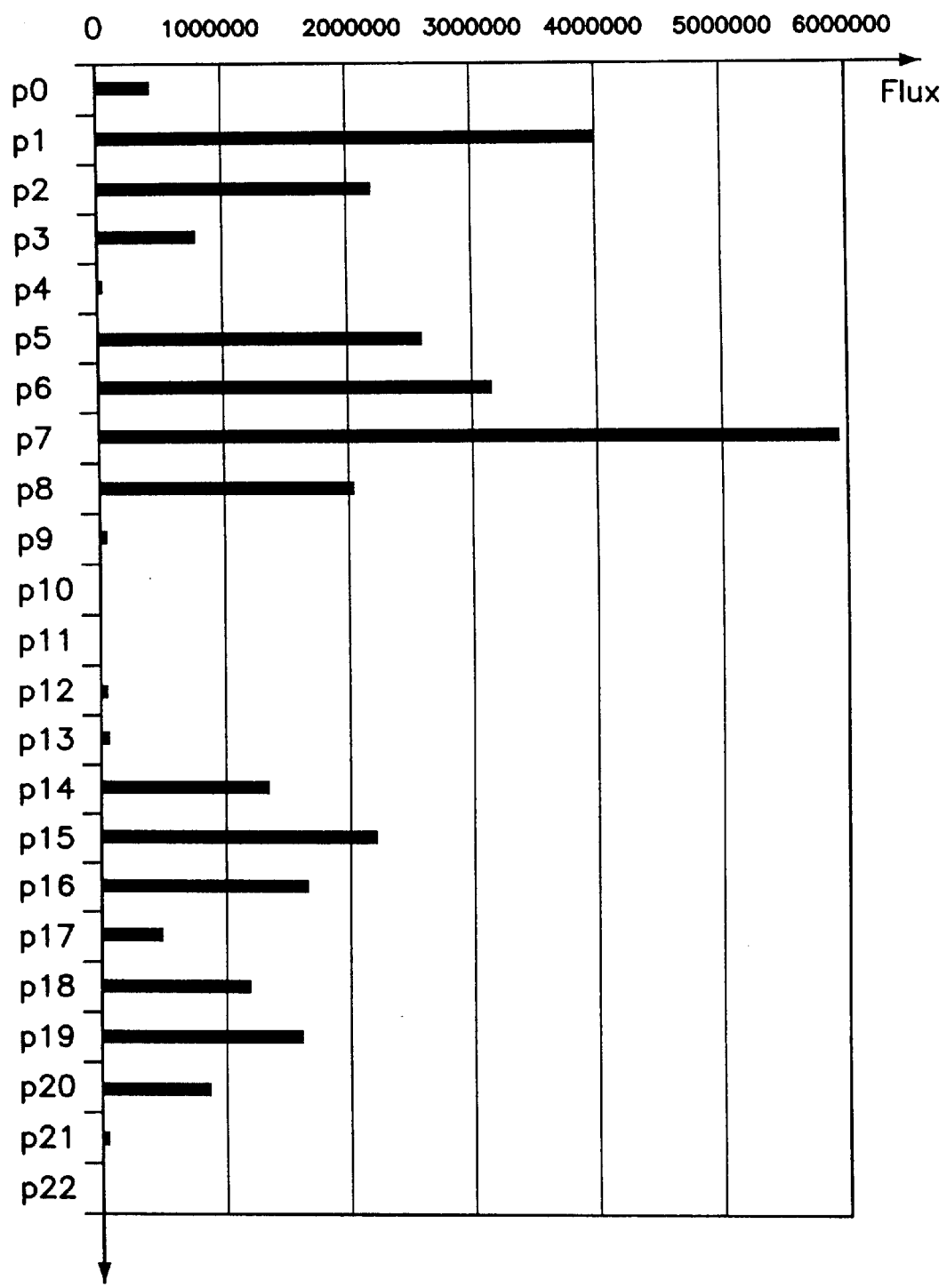
FIG. 3 is a diagram which represents the emission flux values of a series of samples of material as a function of the depth at which the said samples are taken.
Figure 4:
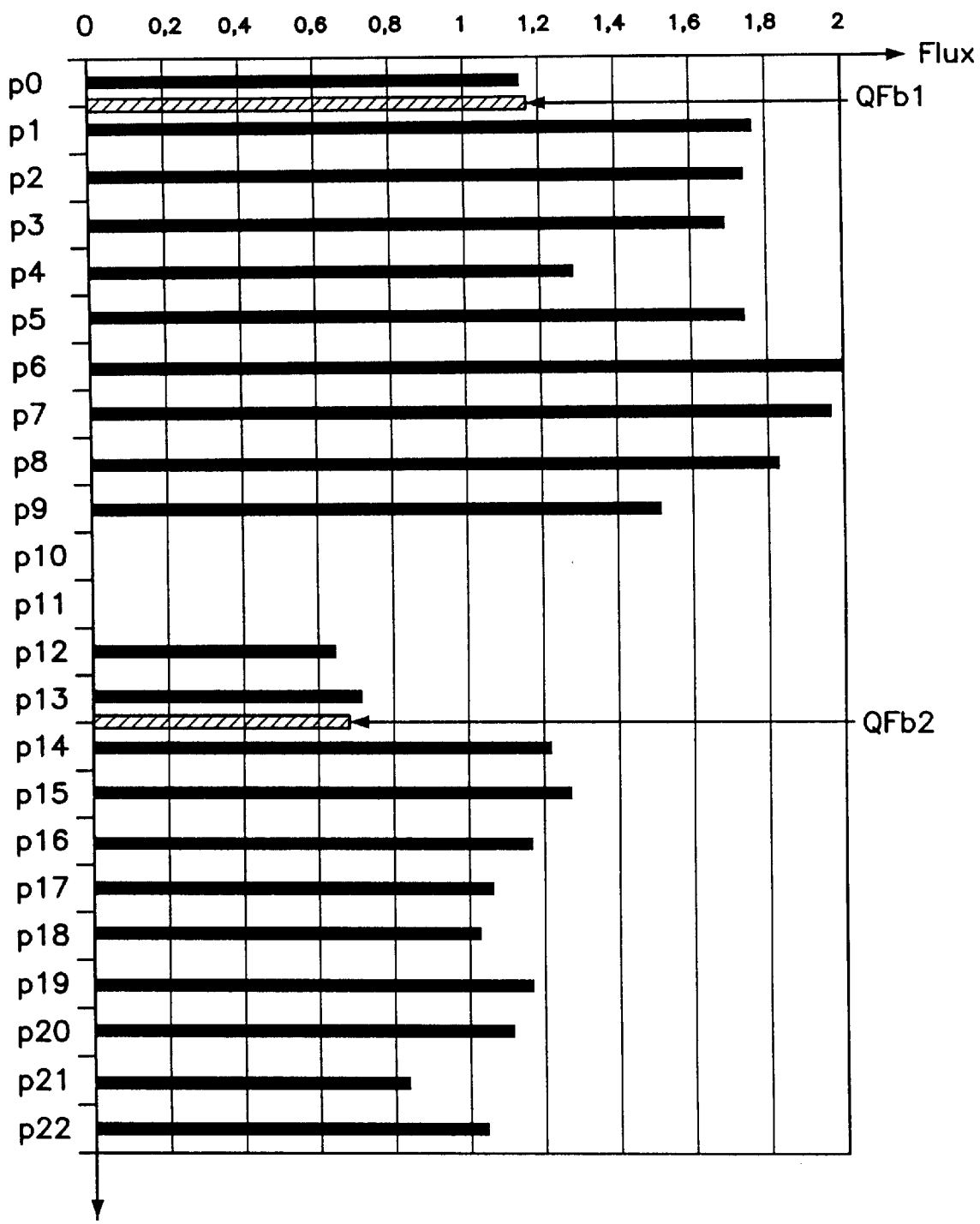
FIG. 4 is a diagram which represents the fluorescence quotient values of a series of samples of material as a function of the depth at which the said samples are taken.

From these values, the diagrams in FIGS. 3 and 4 are plotted, which represent, respectively, the emission flux values (FLUXP) and the fluorescence quotient values (FQp) of the samples of material as a function of the depths at which the core samples were taken.

According to the same procedure, the fluorescence quotient of two samples of reference product, consisting of two samples of mud taken in the course of drilling when this drilling reaches depths of 1790 meters and 2645 meters, is determined.

The following are thus obtained:

TABLE 1

| Reference point p | p in m | dp | FLUXp | Area Ap a | Area Bp b | FQp = a/b |
|---|---|---|---|---|---|---|
| p0 | 1785.20 | 50 | 395,700 | 4,239 | 3,675 | 1.15 |
| p1 | 2019.85 | 167 | 3,988,127 | 15,252 | 8,629 | 1.77 |
| p2 | 2020.70 | 50 | 2,212,750 | 28,098 | 16,157 | 1.74 |
| p3 | 2023.18 | 50 | 781,900 | 9,814 | 5,823 | 1.69 |
| p4 | 2025.50 | 50 | 40,400 | 455 | 353 | 1.29 |
| p5 | 2027.35 | 50 | 2,569,150 | 32,535 | 18,848 | 1.73 |
| p6 | 2028.33 | 50 | 3,211,850 | 42,807 | 21,430 | 2 |
| p7 | 2032.37 | 125 | 5,962,000 | 31,644 | 16,052 | 1.97 |
| p8 | 2033.40 | 50 | 2,029,400 | 26,238 | 14,351 | 1.83 |
| p9 | 2036.35 | 50 | 39,450 | 476 | 313 | 1.52 |
| p10 | 2038.47 | 50 | 1,250 | NS | NS | NS |
| p11 | 2052.50 | 50 | 5,450 | 38 | 71 | 0.54 |
| p12 | 2128.60 | 50 | 26,100 | 203 | 319 | 0.64 |
| p13 | 2382.80 | 50 | 50,250 | 422 | 583 | 0.72 |
| p14 | 2647.60 | 50 | 1,371,850 | 15,069 | 12,367 | 1.22 |
| p15 | 2649.10 | 50 | 2,143,250 | 24,018 | 18,847 | 1.27 |
| p16 | 2650.42 | 50 | 1,669,800 | 18,026 | 15,370 | 1.17 |
| p17 | 2651.45 | 50 | 531,000 | 5,443 | 5,177 | 1.05 |
| p18 | 2652.70 | 50 | 1,160,200 | 11,758 | 11,446 | 1.03 |
| p19 | 2653.50 | 50 | 1,611,900 | 17,411 | 14,827 | 1.17 |
| p20 | 2654.60 | 50 | 824,150 | 8,667 | 7,816 | 1.11 |

TABLE 1-continued

| Reference point p | p in m | dp | FLUXp | Area Ap a | Area Bp b | FQp = a/b |
|---|---|---|---|---|---|---|
| p21 | 2655.53 | 50 | 21,700 | 196 | 237 | 0.83 |
| p22 | 2820.75 | 50 | 9,000 | 92 | 88 | 1.05 | for a depth of 1790 m, a value FQb1=1.18;
for a depth of 2645 m, a value FQb2=0.68.

These values are represented in FIG. 3, between the depths referred to, respectively, as p0 and p1, on the one hand, and p13 and p14, on the other hand.

The table above and the diagrams in FIGS. 3 and 4 reveal two zones A and B of interest in terms of petroleum production.

The final extracts from the samples taken in zone A delimited by the depths 2019.85 m and 2033.40 m are characterized by:

FQp values of between 1.69 and 2.00, which are high relative to the value of 1.18 for the fluorescence quotient FQb1 of the drilling mud used in this zone, except for the depth of 2025.50 m for which FQp is only 1.29.

by emission flux (FLUXP) values of greater than 2,000,000, which are thus very high, except for the depth of 2023.18 m for which the flux value is less than 800,000, and for the depth of 2025.50 m for which the flux value is only 40,400 and thus comparatively very low.

These differences between the fluorescence quotient values of the samples taken at the different depths and the fluorescence quotient value of the sample of mud indicate the presence of formation hydrocarbons in zone A.

The high flux values determined at the same depths indicate that the hydrocarbons detected are present in large amounts in zone A.

The very low flux value for the depth of 2025.50 m indicates that if there are hydrocarbons at that depth, they are in very low amounts.

The samples taken from zone B delimited by the depths 2647.60 m and 2654.60 m are characterized by:

FQp values of between 1.03 and 1.27, which are high relative to the value 0.68 of the fluorescence quotient FQb2 for the drilling mud used in this zone.

emission flux (FLUXP) values of greater than 1,000,000, which are thus high, except for the two samples taken, respectively, at the depths p17 and p20, for which they are greater than 500,000.

These differences between the fluorescence quotient values for the samples taken at the different depths and the fluorescence quotient value for the sample of mud indicate the presence of formation hydrocarbons in zone B.

The high flux values determined at the same depths indicate that the hydrocarbons detected are present in large amounts in zone B.

The flux values in zone A, which are on average higher than those in zone B, reflect a higher concentration of hydrocarbons in zone A than in zone B.

The different values for the fluorescence quotients FQp in zones A and B reflect the different natures of the hydrocarbons present in these zones.

The superiority of the fluorescence quotient values for the samples in zone A relative to those in zone B indicates that the hydrocarbons detected in zone A are heavier than those detected in zone B.

What is claimed is:

1. Process for detecting and characterizing formation hydrocarbons which comprises carrying out the following steps:

taking a sample of material which is representative of the rocks passed through during a drilling operation, taking a determined amount of material to be analysed from the said sample of material, extracting the hydrocarbons contained in the said amount of material to be analysed, using cyclohexane, in order to make up an initial extract, wherein said process further comprises carrying out the following operations:

diluting the initial extract by a factor d in order to obtain a final extract, exciting the final extract with ultraviolet radiation of a wavelength chosen within the band substantially between 250 and 400 nanometers, recording, in a wavelength band L, an emission spectrum resulting from the excitation of the final extract, calculating the emission flux of the sample of material by applying the following formula:

$$FLUX = d * \sum_{i=1}^{n} I(\lambda i)$$

in which

FLUX represents the emission flux of the sample of material $I(\lambda i)$ represents the intensity of the radiation emitted at a wavelength $\lambda i$ of the band L by the final extract, n represents the number of wavelengths of the emission spectrum sampled at a pitch of between 1 and 20 nanometers, and is equal to L divided by the pitch, i ranges from 1 to n, the value of the emission flux of the sample of material is proportional to the concentration of fluorescent elements in the sample of material, calculating the fluorescence quotient of the sample of material using the following formula:

$FQ$=area $A$/area $B$ in which:

FQ represents the fluorescence quotient of the sample of material, area A and area B are calculated, respectively, by the following formulae:

$$Area\ A = \sum_{i=1}^{n} I(\lambda i)$$

$$Area\ B = \sum_{i=1}^{x} I(\lambda i)$$

in which:

$I(\lambda i)$ and n are defined as above, x is an integer between 1 and n, the value of the fluorescence quotient of the sample of material is representative of the nature of the hydrocarbons contained in the sample of material.

2. Process according to claim 1, wherein the wavelength band L is substantially between 280 and 500 nanometers.

3. Process according to claim 1, wherein the value x corresponds to the reference point of a wavelength $\lambda x$ substantially equal to 367 nanometers, which is representative of the cutoff between the spectra emitted, on the one hand, by the monoaromatic and biaromatic hydrocarbons and by a portion of the triaromatic hydrocarbons, and, on the other hand, by the polyaromatic hydrocarbons.

4. Process according to claim 1, wherein a low value for the fluorescence quotient of the sample of material indicates the presence of light hydrocarbons in the said sample and a high value indicates the presence of heavy hydrocarbons.

5. Process according to claim 1, further comprising taking a series of samples of material at different depths during the drilling, determining the fluorescence quotient and the emission flux of each sample, and plotting the curves representing the said fluorescence quotient and the said emission flux as a function of the depths, of the variations of the fluorescence quotient and of the emission flux, thus making it possible, respectively, to characterize the nature of the fluorescent elements and to assess the degree of concentration of the said elements in the series of samples of material.

6. Process according to claim 1, further comprising comparing the fluorescence quotient of at least one sample of material with the fluorescence quotient of at least one sample of reference product determined in the same way as the fluorescence quotient of the sample of material.

7. Process according to claim 6, wherein the sample of reference product consists of a sample of mud taken during the drilling.

8. Process according to claim 7, wherein a fluorescence quotient value for a sample of material which is close to the value of the fluorescence quotient for the sample of mud taken during the drilling indicates the absence of formation hydrocarbons in the sample of material, and a different value indicates a presence, if, furthermore, the value of the emission flux for the sample of material is high.

9. Process for detecting and characterizing formation hydrocarbons which comprises carrying out the following steps:

taking a sample of material which is representative of the rocks passed through during a drilling operation, taking a determined amount of material to be analysed from the said sample of material, extracting the hydrocarbons contained in the said amount of material to be analysed, using a known amount of a solvent for hydrocarbons in order to make up an initial extract, wherein said process further comprises carrying out the following operations:

diluting the initial extract by a factor d in order to obtain a final extract, exciting the final extract with ultraviolet radiation of a wavelength chosen within the band substantially between 250 and 400 nanometers, recording, in a wavelength band L, an emission spectrum resulting from the excitation of the final extract, calculating the emission flux of the sample of material by applying the following formula:

$$FLUX = d * \sum_{i=1}^{n} I(\lambda i)$$

in which

FLUX represents the emission flux of the sample of material $I(\lambda i)$ represents the intensity of the radiation emitted at a wavelength $\lambda i$ of the band L by the final extract, n represents the number of wavelengths of the emission spectrum sampled at a pitch of between 1 and 20 nanometers, and is equal to L divided by the pitch, i ranges from 1 to n, the value of the emission flux of the sample of material is proportional to the concentration of fluorescent elements in the sample of material, calculating the fluorescence quotient of the sample of material using the following formula:

$FQ = \text{area } A/\text{area } B$ in which:

FQ represents the fluorescence quotient of the sample of material, area A and area B are calculated, respectively, by the following formulae:

$$\text{Area } A = \sum_{i=1}^{n} I(\lambda i)$$

$$\text{Area } B = \sum_{i=1}^{x} I(\lambda i)$$

in which:

$I(\lambda i)$ and n are defined as above, x is an integer between 1 and n, the value of the fluorescence quotient of the sample of material is representative of the nature of the hydrocarbons contained in the sample of material; and further comprising taking a series of samples of material at different depths during the drilling, determining the fluorescence quotient and the emission flux of each sample, and plotting the curves representing the said fluorescence quotient and the said emission flux as a function of the depths, of the variations of the fluorescence quotient and of the emission flux, thus making it possible, respectively, to characterize the nature of the fluorescent elements and to assess the degree of concentration of the said elements in the series of samples of material.

* * * * *